United States Patent
Wang et al.

(10) Patent No.: US 8,986,814 B2
(45) Date of Patent: Mar. 24, 2015

(54) SUPERHYDROPHOBIC SURFACES

(75) Inventors: Evelyn N. Wang, Cambridge, MA (US); Matthew McCarthy, Arlington, MA (US); Ryan Enright, Whitestone, NY (US); James N. Culver, Potomac, MD (US); Konstantinos Gerasopoulos, College Park, MD (US); Reza Ghodssi, Silver Spring, MD (US)

(73) Assignees: Massachusetts Institute of Technology, Cambridge, MA (US); University of Maryland, College Park, College Park, MD (US)

( * ) Notice: Subject to any disclaimer, the term of this patent is extended or adjusted under 35 U.S.C. 154(b) by 100 days.

(21) Appl. No.: 13/582,260

(22) PCT Filed: Mar. 4, 2011

(86) PCT No.: PCT/US2011/027321
§ 371 (c)(1),
(2), (4) Date: Nov. 21, 2012

(87) PCT Pub. No.: WO2011/109793
PCT Pub. Date: Sep. 9, 2011

(65) Prior Publication Data
US 2013/0059123 A1 Mar. 7, 2013

Related U.S. Application Data

(60) Provisional application No. 61/310,785, filed on Mar. 5, 2010.

(51) Int. Cl.
B32B 3/30 (2006.01)
B32B 5/00 (2006.01)
C12N 7/00 (2006.01)

(52) U.S. Cl.
CPC ........ *C12N 7/00* (2013.01); *C12N 2770/00031* (2013.01)
USPC ........... 428/164; 428/156; 428/161; 427/402; 427/419.2

(58) Field of Classification Search
USPC ........................... 428/164, 156, 161; 977/802
See application file for complete search history.

(56) References Cited

U.S. PATENT DOCUMENTS

2009/0250588 A1   10/2009   Robeson et al.

FOREIGN PATENT DOCUMENTS

WO   WO 2007/012114   2/2007

OTHER PUBLICATIONS

International Preliminary Report on Patentability dated Sep. 20, 2012 for PCT/US2011/027321.
International Search Report and Written Opinion mailed May 19, 2011 for PCT/US2011/027321.
Naik et al., "International biomimetics," Materials Today, vol. 8, Iss. 9, pp. 18/26, Sep. 2005.
Wei et al., "Template Synthesis of Hierarchically Structured Composites," Advanced Materials, vol. 20, Iss. 15, pp. 2965-2969, 2008.

*Primary Examiner* — Maria Veronica Ewald
*Assistant Examiner* — Laura Auer
(74) *Attorney, Agent, or Firm* — Steptoe & Johnson LLP

(57) ABSTRACT

Surfaces having a hierarchical structure—having features of both microscale and nanoscale dimensions—can exhibit superhydrophobic properties and advantageous condensation and heat transfer properties. The hierarchical surfaces can be fabricated using biological nanostructures, such as viruses as a self-assembled nanoscale template.

14 Claims, 8 Drawing Sheets

SUPERHYDROPHOBIC SURFACES

CLAIM OF PRIORITY

This application claims priority under 35 USC 371 to International Application No. PCT/US2011/027321, filed on Mar. 4, 2011, which claims priority to provisional U.S. Application No. 61/310,785, filed Mar. 5, 2010, each of which is incorporated by reference in its entirety.

FEDERALLY SPONSORED RESEARCH OR DEVELOPMENT

This invention was made with government support under Grant No. CMMI0927693 awarded by the National Science Foundation, under Grant No. DE-FG02-02ER45975 awarded by the Department of Energy and under Contract No. W31P4Q-09-1-0007 awarded by the Army Aviation and Missile Command. The government has certain rights in the invention.

TECHNICAL FIELD

The present invention relates to superhydrophobic surfaces.

BACKGROUND

Superhydrophobic surfaces, with static contact angles greater than 150°, droplet hystereses less than 10°, and roll-off tilt angles typically less than 2°, resist wetting and exhibit self-cleaning properties. Such properties are desirable for coatings on buildings, solar cells, and textiles, as well as drag reduction and increased heat transfer via drop-wise condensation. In nature, a wide array of wetland and aquatic plant leaves exhibit self-cleaning properties and resist wetting upon the impact of rainfall. Due to the abundance of water, these wetland plants do not rely on the intake of moisture through their leaves to hydrate. In fact, their superhydrophobic properties are a necessity for survival. Shedding water from the surface dramatically increases the uptake of $CO_2$ for photosynthesis, and these self-cleaning abilities reduce the formation of bacteria and fungi that would otherwise thrive in such hot moist climates. Significant efforts have focused on mimicking the naturally occurring structures of the lotus leaf, which demonstrates superhydrophobic self-cleaning properties. However, existing fabrication methods have limited the ability to accurately mimic both the surface structures and resulting water-repellent behavior of the lotus under droplet impact.

SUMMARY

Biomimetic surfaces having a hierarchical structure—having features of both microscale and nanoscale dimensions—can exhibit superhydrophobic properties. Such hierarchical surfaces can be fabricated using self-assembled biological nanostructures, such as viruses. Viruses can be genetically engineered to impart desirable properties, such as affinity for a surface. A genetically-modified virus can serve as a nanoscale template for the synthesis of a hierarchically structured surface. The surface can be superhydrophobic, with static contact angles greater than 170°, contact angle hysteresis of less than 2°, and roll-off angles of less than 0.25°. The surface can also exhibit advantageous condensation mass and heat-transfer properties.

In one aspect, a superhydrophobic surface includes a substrate including a plurality of microscale features on a surface of the substrate, wherein the microscale features are elaborated with a plurality of nanoscale features each including a virus.

The virus can include a protein having an affinity for the substrate, the microscale features, or both. The surface can further include a first coating over the surface; the first coating can be metallic. The surface can further include a second coating over the first coating; the second coating can be a metal oxide. The surface can further include a third coating over the second coating; the third coating can be a hydrophobic material.

The virus can be a tobacco mosaic virus. The tobacco mosaic virus can include at least one genetically engineered mutation. The mutation can favor the virus binding perpendicularly to a surface.

The structures can resist pinning droplets impacting the surface, for droplets impacting at a velocity of less than 2.0 m/s, less than 3.0 m/s, or less than 4 m/s.

In another aspect, a method of making a superhydrophobic surface includes forming a plurality of microscale features on a substrate, and elaborating the microscale features with a nanomaterial, wherein the nanomaterial includes a virus.

The virus can include a protein having an affinity for the substrate, the microscale features, or both. The surface can further include a first coating over the surface; the first coating can be metallic. The surface can further include a second coating over the first coating; the second coating can be a metal oxide. The surface can further include a third coating over the second coating; the third coating can be a hydrophobic material.

The virus can be a tobacco mosaic virus. The tobacco mosaic virus can include at least one genetically engineered mutation. The mutation can favor the virus binding perpendicularly to a surface.

Other features, objects, and advantages will be apparent from the description and drawings, and from the claims.

DETAILED DESCRIPTION

Surface Wetting and Hydrophobicity

Figure 1:
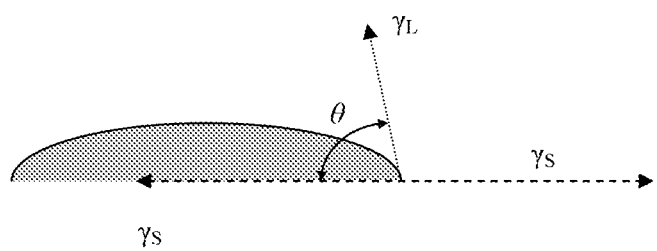
FIG. 1 is a schematic depiction of a droplet on a surface, illustrating relevant properties describing the interaction of the droplet, surface, and air.

At the surface of a liquid is an interface between that liquid and some other medium. How the liquid and the medium interact depends in part on the properties of the liquid, including surface tension. Surface tension is not a property of the liquid alone, but a property of the liquids interface with another medium. Where three phases meet, they form a contact angle, θ, which is the angle that the tangent to the liquid surface makes with the solid surface. A droplet resting on a flat solid surface and surrounded by a gas forms a characteristic contact angle θ often called the Young contact angle. Thomas Young defined the contact angle θ by analyzing the forces acting on a fluid droplet resting on a solid surface surrounded by a gas (see FIG. 1).

$$\gamma_{SG} = \gamma_{SL} + \gamma_{LG} \cos\theta \quad (1)$$

where $\gamma_{SG}$ is the interfacial tension between the solid and gas, $\gamma_{SL}$ is the interfacial tension between the solid and liquid, and $\gamma_{LG}$ is the interfacial tension between the liquid and gas.

Figure 2:
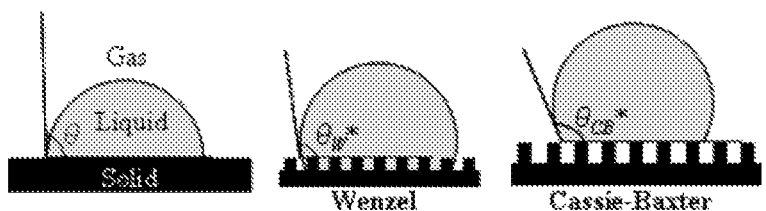
FIG. 2 is a schematic depiction of droplets on flat and textured surfaces.

If the solid surface is rough, and the liquid is in intimate contact with the rugged or featured surface, the droplet is said to be in the Wenzel state. If instead the liquid rests on the tops of the features or rugged surface, it is said to be in the Cassie-Baxter state. Examples of these states are shown in FIG. 2.

Wenzel determined that when the liquid is in intimate contact with a microstructured surface, θ will change to $\theta_{W*}$.

$$\cos\theta_{W*} = r\cos\theta \quad (2)$$

where r is the ratio of the actual area to the projected area. Wenzel's equation shows that a microstructured surface amplifies the natural tendency of a comparable featureless surface. A hydrophobic surface (one that has an original contact angle greater than 90°) becomes more hydrophobic when microstructured. In other words, its new contact angle becomes greater than the original. However, a hydrophilic surface (one that has an original contact angle less than 90°) becomes more hydrophilic when microstructured. Its new contact angle becomes smaller than the original.

Cassie and Baxter found that if the liquid is suspended on the tops of microstructures, θ will change to $\theta_{CB*}$:

$$\cos\theta_{CB*} = \phi(\cos\theta + 1) - 1 \quad (3)$$

where φ is the area fraction of the solid that touches the liquid. Liquid in the Cassie-Baxter state is more mobile than in the Wenzel state.

Contact angle is a measure of static hydrophobicity, while contact angle hysteresis and slide angle are measures of dynamic hydrophobicity. Contact angle hysteresis is a phenomenon that characterizes surface heterogeneity. There are two common methods for measuring contact angle hysteresis: the tilting base method and the add/remove volume method. Both methods allow measurement of the advancing and receding contact angles. The difference between advancing and receding contact angles is called the contact angle hysteresis, and it can be used to characterize surface heterogeneity, roughness, and mobility. Heterogeneous surfaces can have domains which impede motion of the contact line. The slide angle is another dynamic measure of hydrophobicity. Slide angle is measured by depositing a droplet on a surface and tilting the surface until the droplet begins to slide. Liquids in the Cassie-Baxter state generally exhibit lower slide angles and contact angle hysteresis than those in the Wenzel state.

Droplet Condensation and Evaporation

Efficient condensation is required for a range of industrial processes. In particular the efficiency of steam power cycles, thermal-based desalination, and phase-change-based thermal management solutions for electronics cooling are functionally dependent on the condensation behavior of water on mass and heat transfer surfaces. In the 1930's, Schmidt and co-workers identified dropwise condensation (DWC) as a superior mode of mass and heat transfer in comparison to filmwise condensation (FWC) (see Schmidt, E., Schurig, W. and Sellschopp, W. *Tech. Mech. Thermodynamik*, 1, 53-63 (1930), which is incorporated by reference in its entirety). Subsequent investigations found that DWC mass and heat transfer rates could be up to an order of magnitude larger than those associated with FWC. See, for example, Rose, J. W. *Proc Instn Mech Engrs*, Vol 216, Part A: J Power and Energy (2002), which is incorporated by reference in its entirety. This result is associated with the periodic departure of large, thermally-insulating droplets from the surface, typically under the influence of gravity, that allows for the re-growth of smaller droplets with reduced thermal resistance on the exposed areas. Rose and co-workers (id.) have argued that the self-similar distribution of drop sizes is a significant factor governing the overall rate of mass and heat transfer. Under the influence of gravity, the requirement for droplet departure, to first order, is given by Bo=$\rho g d^2/\gamma \geq 1$, where ρ is the condensate density, g is the local acceleration due to gravity, d is the droplet diameter, and γ is the condensate surface tension. For water, this leads to a distribution of droplets ranging in size from the critical nucleus (~1 nm) up to the capillary length (~1 mm). However, recent investigations by Boreyko & Chen (PRL, 2009) Phys. Rev. Lett. 103, 184501 (2009), which is incorporated by reference in its entirety, have demonstrated that the upper drop size can be restricted to less than 100 μm (Bo<$10^{-3}$) via a surface-tension-driven departure mechanism that occurs on nanostructured superhydrophobic surfaces.

Hierarchical Surfaces

Many surfaces which appear smooth to the naked eye are in fact not perfectly smooth when examined at smaller scales, i.e., at the scale of micrometers (microscale) or nanometers (nanoscale). In particular, surfaces which appear flat at the macro scale can have deviations from flatness, i.e., variations above and below an average, macro scale, "flat," 2-dimensional surface. Thus a surface can have 3-dimensional character at the microscale and at the nanoscale.

A surface can include features which extend across both the nanoscale and the microscale. Surfaces having both microscale and nanoscale features can have increased hydrophobicity or hydrophilicity compared to flat surface, or compared to a surface having only microscale or only nanoscale features. Such a surface, having both nanoscale features and microscale features, can be referred to as a hierarchical surface. Microscale features have dimensions of approximately 1 μm or greater, 3 μm or greater, 10 μm or greater, 50 μm or greater, 100 μm or greater, 250 μm or greater, or 500 μm or greater. Microscale features can in some cases extend to greater dimensions; for example, a line-shaped feature might be several μm in width but thousands of μm in length. Despite the length extending beyond the microscale, this line-shaped feature would nonetheless be considered microscaled, because of the μm dimensions of the width.

Nanoscale features have dimensions of approximately 3 μm or smaller, 2 μm or smaller, 1 μm or smaller, or 500 nm or smaller. Nanoscale features can in some cases extend to greater dimensions; for example, a line-shaped feature might be several cm or several mm in length, or less, e.g., several nm in width up to several μm in length. Despite the length extending beyond the nanoscale, this line-shaped feature would nonetheless be considered nanoscaled, because of the nm dimensions of the width.

On a hierarchical surface, microscale features can be elaborated or "decorated" with nanoscale features. For example, a micrometer-scale projection from a surface (e.g., in the shape of a post or pillar) can include a number of nanometer-scale features (e.g., projections, indentations, or other features) on the sides and top of the pillar. Alternatively, on a hierarchical surface, microscale and nanoscale features can be isolated from one another.

As is clear from the preceding description, there is not necessarily a clear diving line between the nanoscale and microscale. Nonetheless, when microscale and nanoscale features are both present on a surface, they are desirably distinct from one another. In other words, when both present on a surface, nanoscale features are necessarily smaller than microscale features. For example, a microscale feature can have at least one dimension (e.g., height, width, depth) which is at least 2 times larger, at least 5 times larger, at least 10 times larger, or more, than does a nanoscale feature.

Features on a surface can form a pattern, e.g., a 2-dimensional pattern, which can be a regular pattern or an irregular pattern. The pattern can be a predetermined pattern, i.e., one that is selected and purposefully constructed or formed. A pattern can include sub-patterns, for example, when a number of small elements, considered together, form a larger element; or when a pattern includes two patterns interleaved or interspersed with one another. In other words, a pattern can exist across different size scales. A regular pattern can be characterized by repetition: for example, a single structure of defined size and shape, occurring at regularly spaced intervals. Such a pattern can be characterized by the size and shape of the structure, the spacing between the structures, and the geometric relationship between adjacent structures (e.g., translations, rotations, reflections, and combinations of these). A regular 2-dimensional pattern can be characterized according to which of the seventeen possible plane-symmetry groups to which it belongs. Features on a surface can also be arranged irregularly, i.e., without regard to a fixed pattern.

As described above, it is know from the work of Wenzel and Cassie that microscaled features on surfaces increase the hydrophobicity of the surface relative to a flat surface. A combination of nano- and micro-scaled features can lead to further increases in the hydrophobicity of a surface. For example, depending on the material composition of the surface, a dual-scale surface can have a water contact angle which is larger than that of a comparable flat surface by 30° or more, 40° or more, or 50° or more. A dual-scale surface can have a water contact angle which is larger than that of a comparable single-scale featured surface (i.e., one having only microscale features or only nanoscale features) by 10° or more, 20° or more, or 30° or more.

Fabrication of Hierarchical Surfaces

A hierarchical surface can be made by forming a plurality of microscale features on a substrate (e.g., a substrate having a flat surface), and subsequently elaborating the microscale features with a plurality of nanoscale features. Forming the microscale features can include adding or removing material from the surface; likewise, elaborating the microscale features can include adding or removing material. When material is added, it can be the same material or a different material than the underlying surface. Some techniques for making hierarchical surfaces include direct molding (see, e.g., and Jeong, H. E., et al., *Langmuir* (2006) 22, 1640), etching (see, e.g., Kwon, Y., et al., *Langmuir* (2009) 25(11), 6129, and Chen, M. H., et al., *Appl. Phys. Letters* (2008) 95, 023702), deposition (see, e.g., Bhushan, B., et al., *Appl. Phys. Letters* (2008) 93, 093101), and growth (see, e.g., Liu, X., et al., *Langmuir* (2009) 25(19), 11822, and Kim, H., et al., *J. Micromech. Microeng.* (2009) 19, 095002) techniques. Each of the above references is incorporated by reference in its entirety.

Elaborating the microscale features can include adhering a nanomaterial to the microscale features. A nanomaterial is a material composed of nanoscale particles, including, for example, fullerenic materials (e.g., fullerenes and carbon nanotubes), semiconductor nanocrystals (e.g., quantum dots or semiconductor nanowires), metallic nanoparticles, ceramic nanoparticles, polymer nanoparticles, and biological nanomaterials. Biological nanomaterials include, for example, viruses. Viruses generally include a protein coat surrounding viral genetic material (DNA or RNA), and, in some cases, a lipid envelope surrounding the protein coat. Viruses have a wide variety of morphologies; they can be roughly spherical (e.g., icosahedral), elongated (e.g., rod-shaped), or more complex (e.g., having an icosahedral "head" and an elongated "tail," as in the T4 bacteriophage).

Once the microscale and nanoscale features have been formed, the surface can be coated with one or more coating layers. The coating layers can be selected to impart desired properties on the surface, such as, for example, mechanical robustness and increased hydrophobicity.

One suitable substrate is a silicon wafer. Techniques for forming microscale and nanoscale features on silicon surfaces are well known. One such technique is to apply a layer of photoresist resin, selectively cure areas of the layer (e.g., using a patterned mask), and then remove the uncured photoresist. Choice of the mask pattern and layer thickness determines the size and shape of the resulting features. As discussed above, the pattern can be in a wide variety of forms. One example of a suitable pattern is a regular array of posts.

The microscale pattern is then elaborated with nanoscale features, for example by contacting the surface with a nanomaterial which adheres to the surface, e.g., a virus having an affinity for the material(s) that compose the surface. An initial coating layer, e.g., a metallic layer can be deposited by (for example) electroless plating. The metallic layer can be further coated with a metal oxide, e.g., alumina ($Al_2O_3$), by (for example) atomic layer deposition. The metal and metal oxide layers can provide mechanical robustness and a favorable surface for a further coating with a hydrophobic material; e.g., a hydrophobic polymer or hydrophobic silane. The hydrophobic material can include hydrocarbon (e.g., a saturated hydrocarbon) groups, halohydrocarbon groups (e.g., a saturated fluorohydrocarbon), or halocarbon groups (e.g., a perfluorinated alkyl group). In one example, the hydrophobic material can be (tridecafluoro-1,1,2,2-tetrahydrooctyl)-1-trichlorosilane, deposited by exposing the surface to a vapor of the hydrophobic material.

A method for creating biomimetic hierarchical surfaces based on the Tobacco mosaic virus (TMV) has been implemented to study the role of length scales on the anti-wetting behavior of superhydrophobic surfaces. TMV is a plant virus, measuring 300 nm in length and 18 nm in diameter. It is benign to humans and can be genetically engineered to have enhanced binding properties. TMV having specifically engineered functional groups at predetermined locations enables self-assembly and directed patterning over a wide range of materials (metals, ceramics and polymers) and geometries.

The TMV is a well-studied biological material and has been demonstrated in the development of nanowires as well as high surface-area electrode surfaces for energy storage (E. Royston et al., *Langmuir* 24, 906 (2008); E. Royston et al., *J. Coll. And Inter. Science* 332, 402 (2009), and K. Gerasopoulos et al., *J. Micromech. Microeng.* 18, 104003 (2008), each of which is incorporated by reference in its entirety). Each TMV structure consists of approximately 2130 coat protein subunits wrapped around a ribonucleic acid ((+)-ssRNA) in a helical structure. The introduction of cysteine residues (amino acids with thiol groups) within the virus coat protein open reading frame results in viral structures 300 nm in length and 18 nm in diameter with enhanced binding properties based on a strong covalent-like interactions (K. Gerasopoulos et al., *J. Micromech. Microeng.* 18, 104003 (2008), which is incorporated by reference in its entirety). Each virus contains a helical pattern of cysteine residues along the entire length of the virus. These cysteines are recessed within the protein structures, while a single cysteine at the :3' end of the virus is exposed. Accordingly, the favorable attachment of the TMV is perpendicular to the assembly surface through the single cysteine at the end of each virus. This is because the cysteines of the virus outer surface are recessed within the grooves of the helical structure and therefore not directly exposed during assembly. They are, however, exposed to aqueous solutions used to catalyze and electroplate the surfaces. The resulting nanostructure is a highly textured three-dimensional scaffolding of TMV conformally coated with metal. The virus is fully encased and no longer plays a role defining or maintaining the nanostructured surface thereafter.

EXAMPLES

Surface Fabrication

A photo-definable negative resist (SU-8 10, Microchem) was spin-coated to a thickness of 15 μm on a silicon wafer and exposed to create micropost arrays. The wafer was then diced into individual 2 cm×2 cm die. The die were placed in a phosphate buffer solution (pH 7) containing the tobacco mosaic virus (TMV) at a concentration of 0.1 mg/mL and allowed to incubate overnight while the virus self-assembled on the exposed silicon and SU-8 surfaces. After TMV assembly, the surface-exposed cysteines residues of the virus were activated with a palladium catalyst in a solution prepared by mixing a palladium salt with phosphate buffer. The samples were then coated with nickel in an electroless plating solution in which they were immersed for 3-5 minutes. The catalyst solution was prepared by dissolving 29 mg of $NaPdCl_4$ in 10 mL of DI water. The nickel plating solution was prepared by mixing 0.6 g $NiCl_2$, 0.45 g glycine, 1.5 g $Na_2B_4O_7$, 0.77 g DMAB and 25 mL of DI water and stirring until solution reached pH 7.

After metallization, the surfaces were functionalized through atomic layer deposition (ALD) of $Al_2O_3$ followed by vapor-phase deposition of silane to achieve superhydrophobic properties. A uniform 15 nm thick $Al_2O_3$ was deposited using alternate pulse sequences of trimethyl aluminum and $H_2O$ at 220° C. and a deposition rate of 0.1 nm/cycle. ALD provided excellent uniformity and a coating conformal to the nanoscale features of the virus. A silane monolayer was formed onto the $Al_2O_3$ surface at room temperature with the samples exposed to vapor-phase (tridecofluoro-1,1,2,2-tetrahydrooctyl)-1-trichlorosilane for 40 minutes.

Figure 3:
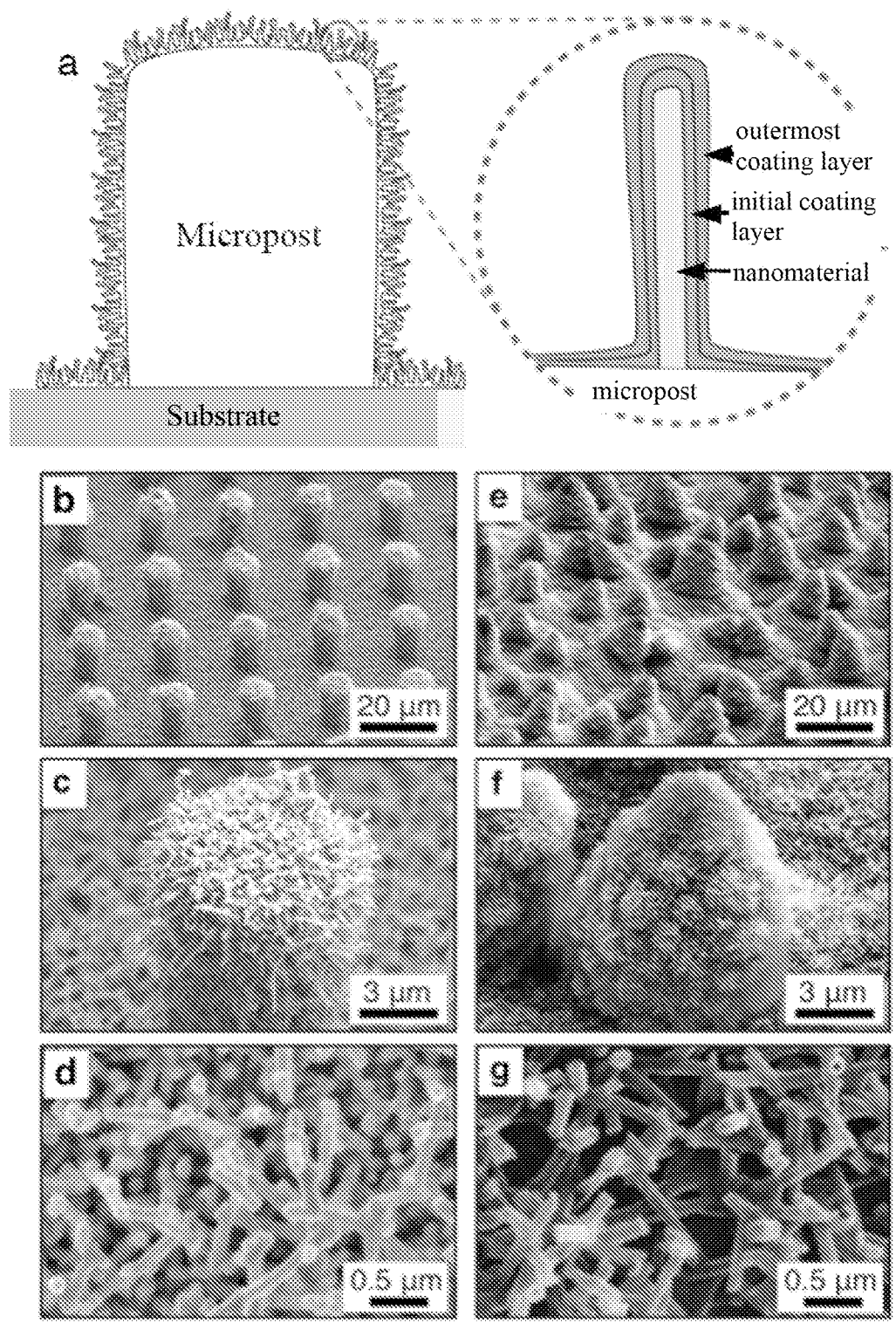
FIG. 3A is schematic depiction of a hierarchical surface.
FIGS. 3B-3D are micrographs of biomimetic hierarchical surfaces.
FIGS. 3E-3G are micrographs of biological hierarchical surfaces.

FIG. 3A shows a cross-sectional schematic of the resulting micro- and nano-scale surface structures while FIGS. 3B-3G provide a side-by-side comparison of the biomimetic (FIGS. 3B-3D) and naturally occurring (FIGS. 3E-3G) surfaces at various length scale (see, e.g., K. Koch, et al., *Prog. in Mat. Science* 54, 137 (2009), which is incorporated by reference in its entirety). As can be seen, self-assembly of the TMV provided consistent and conformal coverage of the polymer microstructures.

Figure 4:
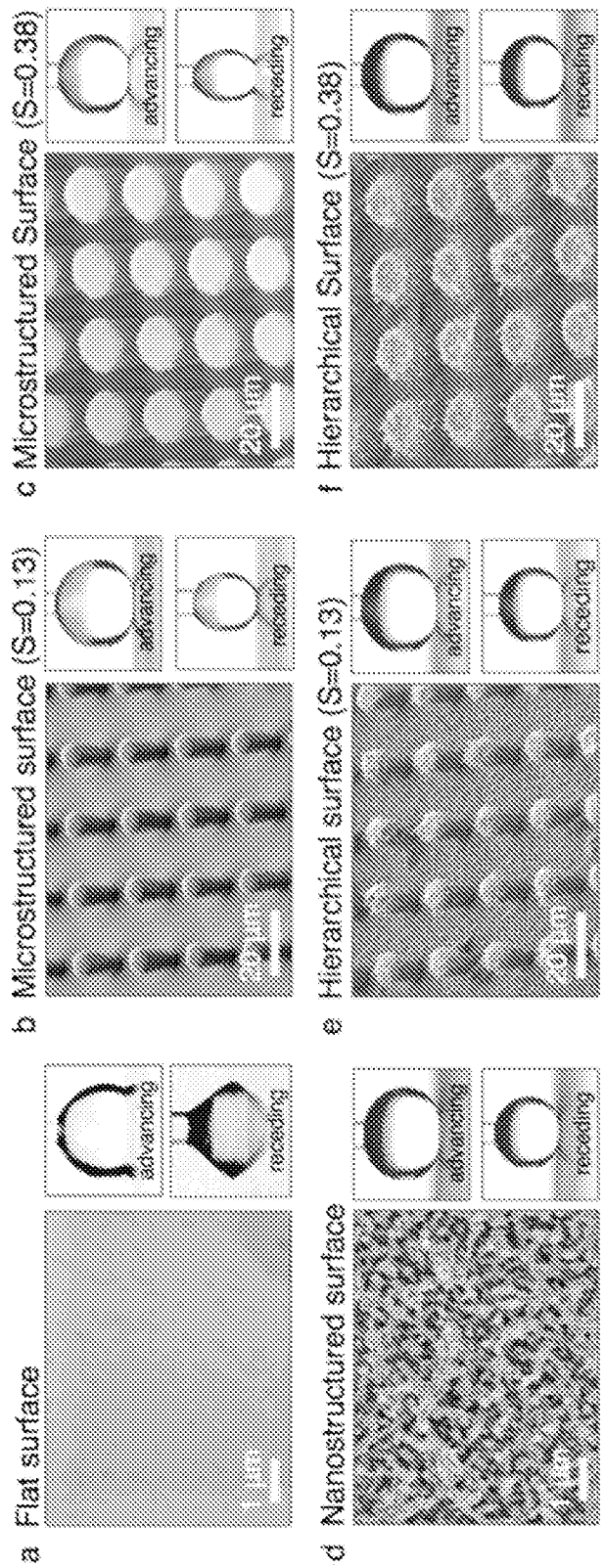
FIGS. 4A-4F show micrographs of a flat surface (4A), microstructured surfaces (4B-4C), a nanostructured surface (4D), and hierarchical surfaces (4E-4F), along with images of droplets in contact with the surfaces, illustrating the differences in advancing and receding contact angles for the different surfaces.

FIGS. 4A-4F shows the micro- and nano-structure of six different surfaces fabricated as above. Flat surfaces both with (FIG. 4D) and without (FIG. 4A) viral nanostructures, as well as microstructured (FIGS. 4B-4C) and hierarchically structured (FIGS. 4E-4F) surfaces with two different solid fractions, were synthesized and experimentally characterized. The solid fraction of the surfaces was calculated as $S=\pi d^2/4L^2$, where d and L are the pillar diameter and center-to-center spacing, respectively. In FIGS. 4B and 4E, posts were 15 μm tall spaced 20 μm apart, d=μm, S=0.13. In FIGS. 4C and 4F, posts were 15 μm tall spaced 20 μm apart, d=14 μm, S=0.38.

Contact Angle Measurements

Droplet contact angle measurements and droplet impingement imaging were obtained using a high-speed camera (Phantom v7.1, Vision Research) and image-processing software (ImageJ). A micropump and controller (Micro4 Syringe Pump, World Precision Instruments) was used to dispense and control water droplets.

Contact angle hysteresis is defined as the difference between the advancing and receding contact angles, and the roll-off tilt angle is the angle of a tilted surface at which a droplet will roll off. These three values are inter-related and collectively used to determine a surface's ability to demonstrate self-cleaning behavior.

Figure 5:
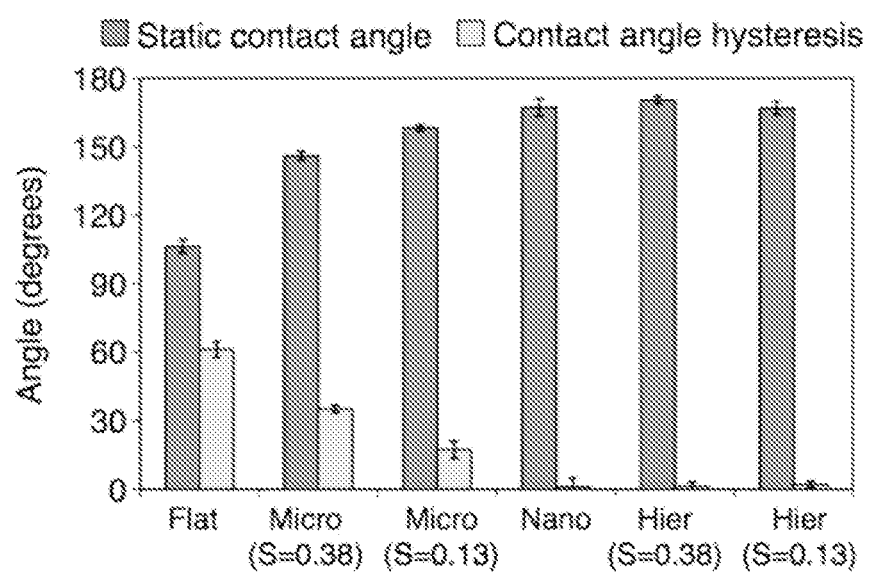
FIG. 5 is a graph depicting static contact angles and contact angle hysteresis values for different surfaces.

Static contact angle measurements were obtained by applying single 10 μL, droplets to the sample surface and evaluating the apparent contact angle using image processing software. Advancing and receding contact angles were measured by increasing and decreasing the volume of a droplet on the sample surfaces while capturing images. The nanostructured and hierarchical surfaces demonstrated roll-off angles below the accuracy of the measurement capabilities (<0.25°), and at no time during the testing of these surfaces could a droplet be maintained in static equilibrium. Accordingly, the static contact angle for nanostructured and hierarchical surfaces was taken to be the average of the advancing and receding contact angles. This is an acceptable approximation as the contact angle hysteresis was smaller than the accuracy of the measurement method. Results for static contact angle and contact angle hysteresis are shown in FIG. 5 for each fabricated sample. Both the nanostructured and hierarchical surface were superhydrophobic with static contact angles over 170° and hystereses less than 2°.

These results raise interesting questions about the need for hierarchical structures in superhydrophobic water-resistant surfaces. If superhydrophobicity can be achieved with nanoscale features alone, why do self-cleaning aquatic and wetland plant leaves invariably have hierarchical surface structures? See, e.g., K. Koch, et al., *Prog. in Mat. Science* 54, 137 (2009), which is incorporated by reference in its entirety. The answer lies in the role of each length scale on water-repellency under droplet impact.

Droplet Impact Wetting

The relationship between contact angle and surface roughness is predicted by the theories of Cassie and Baxter, and Wenzel. Cassie and Baxter's theory governs the behavior of static droplets resting on top of the surface roughness. Vapor pockets are present underneath the liquid resulting in a composite liquid-vapor-solid interface. In Wenzel's model, the droplet has completely penetrated the roughness and no vapor pockets are present. A droplet in the Wenzel state pins to the surface structures and resists droplet motion. While the Cassie state is statically stable, a droplet can be forced into the Wenzel state by overcoming an energy barrier that exists between the two states. This transition from the Cassie to the Wenzel state can occur during droplet impact, and can hamper to self-cleaning properties. As such, the dynamics of impingement, i.e., how droplets interact with a surface when contacting them at speed, as a droplet impacting a surface, can be crucial for robust self-cleaning surfaces.

Figure 6:
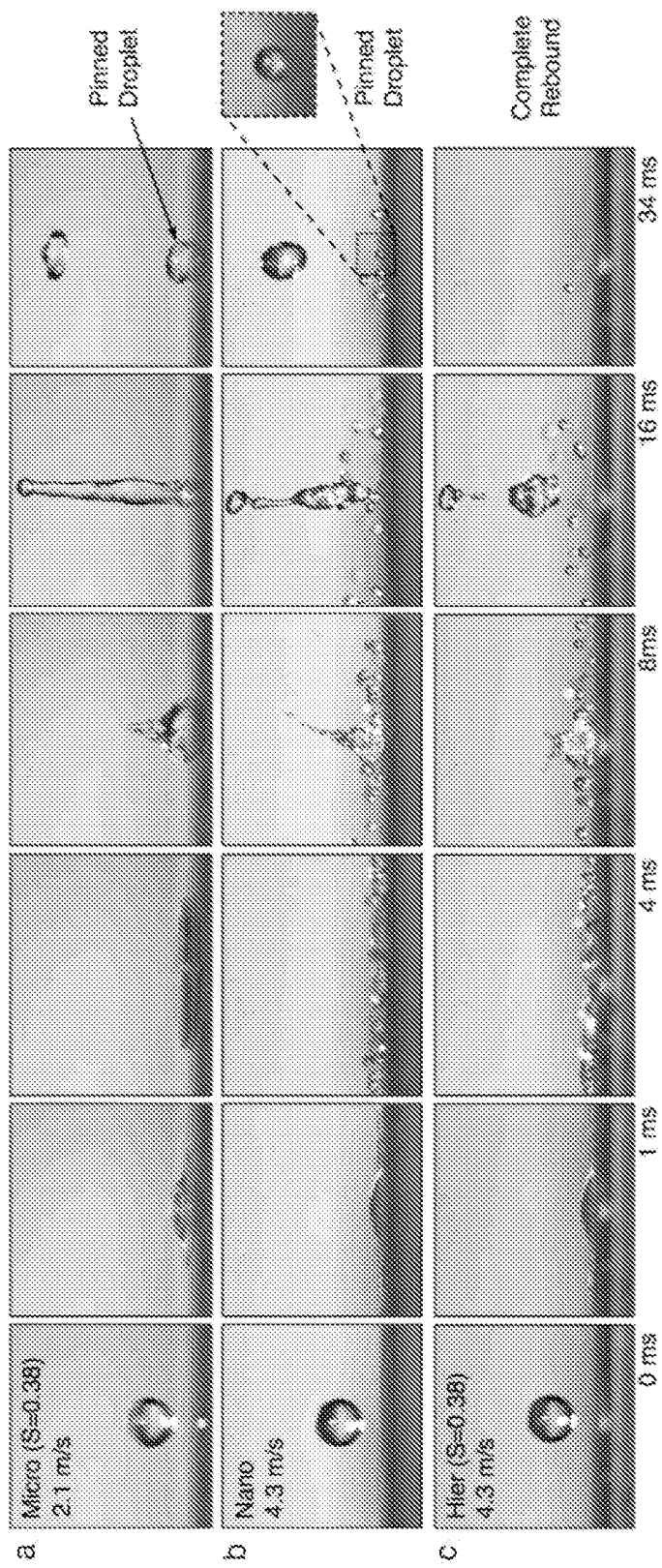
FIGS. 6A-6C show time-series photographs of droplet impingement on different surfaces.

To study the role of dual length scales on droplet impingement, 10 µL, droplets (2.7 mm diameter) were dropped from heights of 0.5-100 cm on each sample, resulting in impact velocities of 0.2-4.3 m/s. A time series of high speed images of droplet impacts on various surfaces are shown in FIGS. 6A (microstructured surface, S=0.38 as in FIG. 4C; impact velocity 2.1 m/s), 6B (nanostructured surface as in FIG. 4D; impact velocity 4.3 m/s), and 6C (hierarchical surface, S=0.38, as in FIG. 4F; impact velocity 4.3 m/s). The microstructured surface showed partial droplet rebound and partial droplet pinning. The nanostructured surface showed partial wetting and break-up into satellite droplets. The hierarchical surface showed complete rebound and break-up into satellite droplets.

Figure 7:
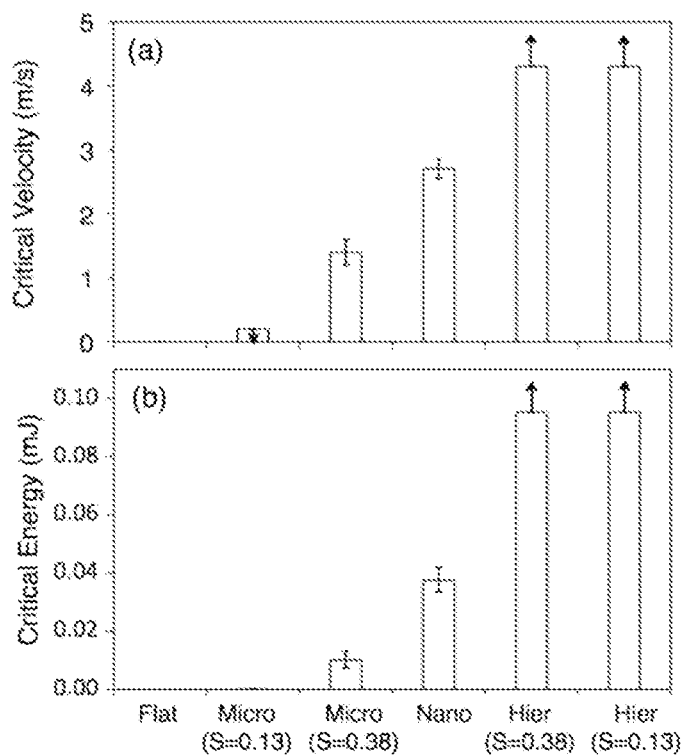
FIGS. 7A-7B are graphs depicting the critical impact velocity ($V_C$) and critical impact energy ($E_C$), respectively, required for wetting of different surfaces.
Figure 8:
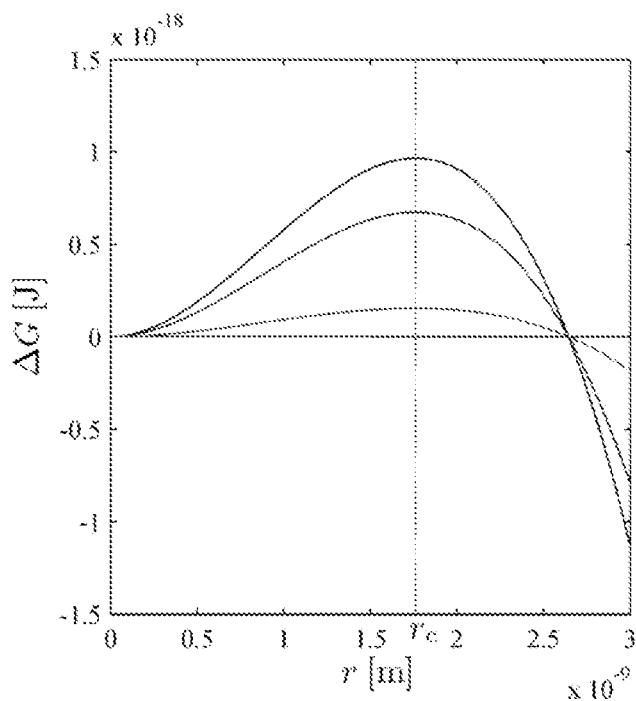
FIG. 8 is a graph illustrating Gibbs free-energy profiles for dropwise condensation under different conditions.

FIG. 7A shows the critical impact velocity, $V_C$, at which wetting of a surfaces is first observed. At speeds higher than this value, the droplet (or some fraction of the droplet) remains attached, signifying a transition to the Wenzel state. FIG. 7B shows the critical kinetic energy, $E_C$, of the droplet at which transition is first observed, defined as $$E_C = 0.5 m V_C^2 \quad (7)$$

where m is the mass of the droplet.

The microstructured surfaces wet at relatively low critical velocities while the nanostructured surface transitioned to a wetted state at a critical velocity of 2.7 m/s. FIGS. 6A-6B show high-speed images of droplets impacting microstructured (S=0.38) and nanostructured surfaces above their critical velocities. Transition was seen for both; a large pinned droplet remained on the microstructured surface for a velocity of 2.1 m/s, and a small pinned droplet remained on the nanostructured surface for a velocity of 4.3 m/s.

The hierarchical surface showed complete rebound and breakup of the impinging droplets for all achievable speeds (FIG. 6C). While the critical velocities of the hierarchical surfaces have not been determined, it can be seen that the critical kinetic energy for the hierarchical transition is notably higher than the sum of its nano and microscale components (FIG. 7B). For the maximum speed tested (4.3 m/s), the critical kinetic energy for hierarchical transition was shown to be at least twice as large as the sum of $E_C$ for the microstructured and nanostructured surfaces.

These counterintuitive results can be explained by considering the effects of compressibility on the impact pressure of impinging droplets. As a spherical droplet impacts a perfectly flat surface, a compressible no-flow region is generated in the droplet, resulting in large pressures associated with the compressed fluid (see, for example, O. G. Engel, *J. Appl. Phys.* 44, 692 (1973), which is incorporated by reference in its entirety). This compressibility event occurs over a circular area on the order of tens of micrometers for millimeter-scale droplets falling at terminal velocities. This critical length scale is identically matched by the microscale component of hierarchical structures found in aquatic and wetland plants and suggests that each length scale (micro and nano) plays a distinct role in water repellency under droplet impact. It is proposed here that, in the hierarchical structures, the microstructures had a destructive effect on the generation and propagation of the large pressures associated with compression, while the nanostructures provide a large antiwetting Laplace pressure resisting transition to a wetted state.

Dropwise Condensation

In addition to biomimetic self-cleaning behaviors, robust superhydrophobic surfaces can be implemented for the enhancement of condensation mass and heat transfer rates. During the condensation process, water vapor changes phase into liquid on a sub-cooled surface. The liquid water forming on this surface results in an increased thermal resistance between it and the condensing vapor, which can greatly reduce the heat transfer coefficient of the process. Superhydrophobic surfaces are promising for the realization of dropwise condensation mass and heat transfer, where the condensing liquid does not wet the interface but instead forms into small droplets that roll off of the surface. This eliminates the existence of an insulating water film and has the potential to increase heat transfer coefficients by a factor of ten.

Figure 9A:
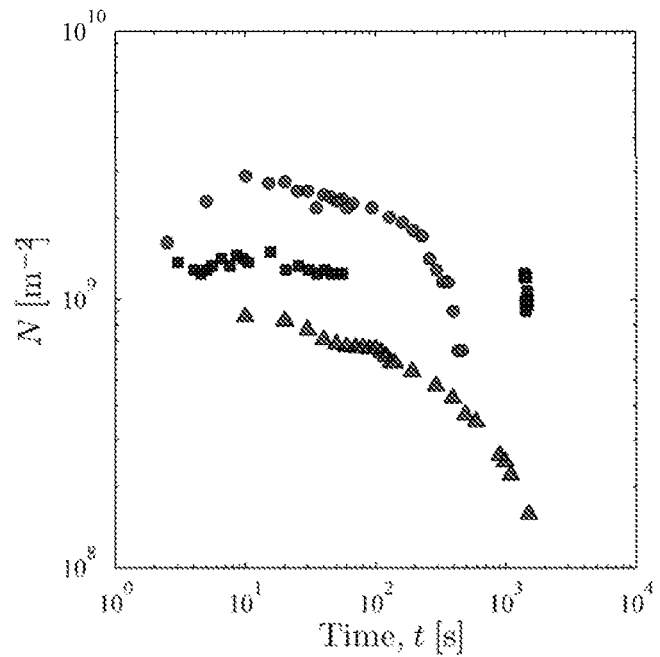
FIGS. 9A and 9B are graphs depicting droplet density and average droplet diameter, respectively, during condensation on different surfaces.
Figure 9B:
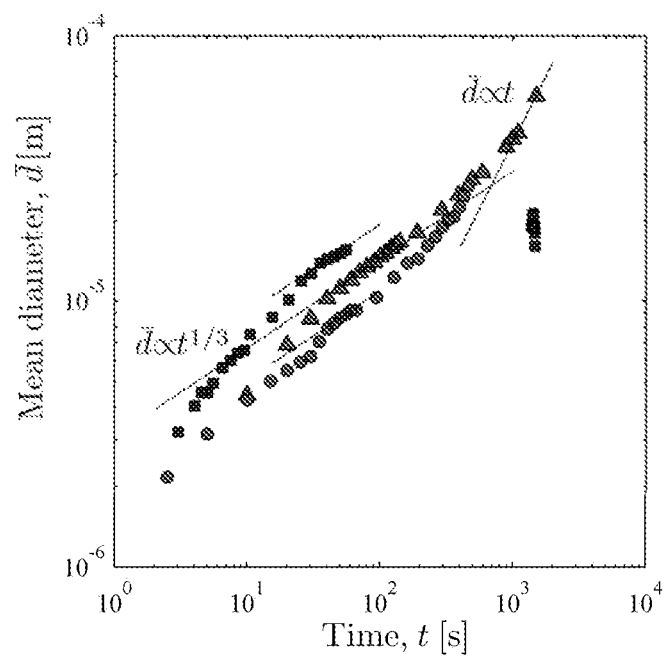

Droplet growth behavior was observed microscopically under controlled conditions, and measurements of average droplet diameter and density as a function of time were recorded. The data for hierarchical surfaces are presented in FIGS. 9A-9B and compared to a smooth hydrophobic surface under the same conditions. These figures show droplet density (FIG. 9A) and average droplet diameter (FIG. 9B) as a function of time on the TMV, TMV-PVA, and a smooth silanated surface. The surface temperature was maintained at a constant $T_s$=283 K and subjected to a water-saturated $N_2$ gas stream at a temperature of $T_v$=293 K and a flowrate, Q=0.15 m³/hr. The apparent nucleation density was ~37% larger on the hierarchical surface than on the chemically similar smooth surface. This may be explained by considering the following geometric argument. On the smooth hydrophobic surface, $f(\theta)$ is determined primarily by the chemical composition of the surface. On the hierarchical surface, however, the nanostructures can provide preferential nucleation sites. Considering a simple corner geometry it can be shown that the shape factor on a silanated surface decreases from $f(\theta)$=0.7 to $f(\theta)$=0.55, a reduction in the nucleation energy barrier of ~21%. The number of preferential nucleation sites found on the TMV surface per unit area can be estimated as $\phi_s/\pi d^2 \approx 10^{12}$ m$^{-2}$, which is three orders of magnitude larger than the experimentally observed initial nucleation density on the TMV surface. Thus, the TMV surface demonstrated nucleation characteristics corresponding to a smooth surface with increased wettability, while maintaining the requirements for surface tension driven droplet departure.

Initially, the average droplet diameter was found to approach the well-known direct growth scaling, $d \propto t^{1/3}$ after a mixed-growth period associated with clustering during initial nucleation.

Figure 10:
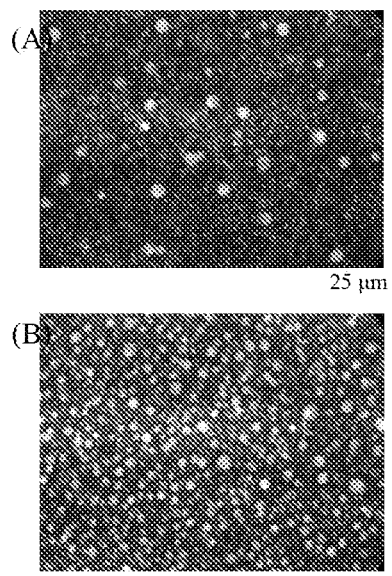
FIGS. 10A and 10B are micrographs illustrating initial nucleation behavior and regrowth behavior, respectively, of droplets on a hierarchical surface.

FIGS. 10A and 10B are micrographs showing initial nucleation (FIG. 10A) and re-growth (FIG. 10B) behavior of droplets on the TMV surface at t=30 s. The initial nucleation density, $N_i$=1.59×10$^9$ m$^{-2}$, was an order of magnitude smaller than the re-growth density, $N_r$=1.42×10$^{10}$ m$^{-2}$, due to the phenomena of site activation, whereby trapped liquid on the TMV surface decreased the energy barrier to condensation.

Figure 11:
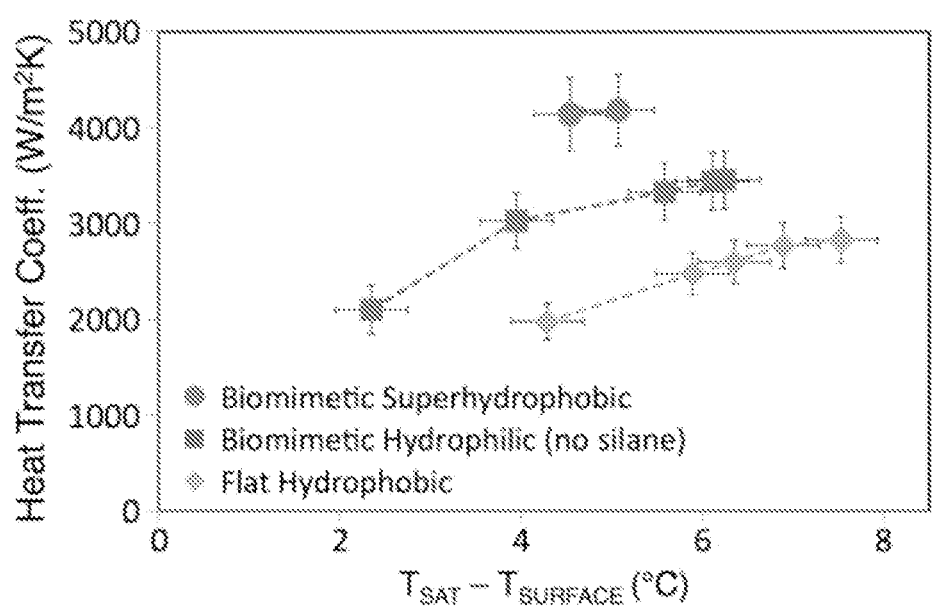
FIG. 11 is a graph showing heat transfer coefficients measured under condensation conditions for different surfaces.

The condensation mass and heat transfer performance of the hierarchical structures was evaluated by exposing the surface to a jet of water vapor while controlling the backside temperature using a thermoelectric module and active cooling. FIG. 11 shows preliminary experimental results for the hierarchical and flat surfaces. A two-fold increase in heat transfer coefficient was observed for the superhydrophobic surfaces as compared to flat samples with identical surface chemistries.

Other embodiments are within the scope of the following claims.

What is claimed is:

1. A superhydrophobic surface comprising:
a substrate including a plurality of microscale features on a surface of the substrate, wherein the microscale features are elaborated with a plurality of nanoscale features each including a virus.

2. The surface of claim 1, wherein the virus includes a protein having an affinity for the substrate, the microscale features, or both.

3. The surface of claim 1, further comprising a first coating over the surface.

4. The surface of claim 3, wherein the first coating is metallic.

5. The surface of claim 4, further comprising a second coating over the first coating.

6. The surface of claim 5, wherein the second coating is a metal oxide.

7. The surface of claim 6, further comprising a third coating over the second coating.

8. The surface of claim 7, wherein the third coating is a hydrophobic material.

9. The surface of claim 1, wherein the virus is a tobacco mosaic virus.

10. The surface of claim 9, wherein the tobacco mosaic virus includes at least one genetically engineered mutation.

11. The surface of claim 10, wherein the mutation favors the virus binding perpendicularly to a surface.

12. The surface of claim 1, wherein the surface resists pinning droplets impacting the surface for droplets impacting at a velocity of less than 2.0 m/s.

13. The surface of claim 12, wherein the surface resists pinning droplets impacting the surface for droplets impacting at a velocity of less than 3.0 m/s.

14. The surface of claim 12, wherein the surface resists pinning droplets impacting the surface for droplets impacting at a velocity of less than 4.0 m/s.

* * * * *